(12) United States Patent
Segond et al.

(10) Patent No.: US 9,114,115 B2
(45) Date of Patent: Aug. 25, 2015

(54) COMPOSITIONS FOR SKIN DISEASE OR DISORDERS

(71) Applicant: BAYER CONSUMER CARE AG, Basel (CH)

(72) Inventors: Caroline Segond, Labastide-Monréjeau (FR); Francoise Chanteloube, Pau (FR); Alain Loiseau, Bouillon (FR); Virginie Petit, Pau (FR); Eric Theron, Montardon (FR)

(73) Assignee: Bayer Consumer Care AG, Basel (CH)

( * ) Notice: Subject to any disclaimer, the term of this patent is extended or adjusted under 35 U.S.C. 154(b) by 0 days.

(21) Appl. No.: 13/674,060

(22) Filed: Nov. 11, 2012

(65) Prior Publication Data

US 2013/0071502 A1    Mar. 21, 2013

Related U.S. Application Data

(63) Continuation of application No. 13/065,996, filed on Apr. 4, 2011, now abandoned.

(30) Foreign Application Priority Data

| Oct. 2, 2008 | (EP) | 08290925 |
| Jan. 13, 2009 | (EP) | 09290027 |
| May 7, 2009 | (EP) | 09290332 |

(51) Int. Cl.

| A61K 36/00 | (2006.01) |
| A61K 36/185 | (2006.01) |
| A61K 8/97 | (2006.01) |
| A61K 8/49 | (2006.01) |
| A61K 8/60 | (2006.01) |
| A61Q 19/00 | (2006.01) |

(52) U.S. Cl.
CPC .............. *A61K 36/185* (2013.01); *A61K 8/498* (2013.01); *A61K 8/602* (2013.01); *A61K 8/97* (2013.01); *A61Q 19/00* (2013.01); *A61Q 19/002* (2013.01); *A61K 2800/75* (2013.01); *A61K 2800/78* (2013.01)

(58) Field of Classification Search
None
See application file for complete search history.

(56) References Cited

U.S. PATENT DOCUMENTS

2003/0175234 A1*  9/2003  Hernandez et al. .............. 424/74

FOREIGN PATENT DOCUMENTS

| EP | 0648496 A1 | 4/1995 |
| JP | 59044313 A  * | 3/1984 |
| JP | 60208908 A  * | 10/1985 |
| JP | 2007-186457 A | 7/2007 |
| WO | 2005077349 A1 | 8/2005 |

OTHER PUBLICATIONS

Domingo et al., "Anti-angiogenic effects of epigallocatechin-3-gallate in human skin," Int. J. Clin. Exp. Pathol., vol. 3, No. 7, pp. 705-709 (2010).
International Search Report for PCT/EP2009/007051, Apr. 8, 2010.
Louis Bouton, "Plantes Medicinales De Maurice (Deuxieme Edition)," p. 124, Jan. 1, 1864.
Melle Amelie Lhuillier, "Contribution a L'Etude Phytochimique De Quatre Plantes Malgaches: Agauria Salicifolia Hook.F Ex Oliver, Agauria Polyphylla Baker (Ericaceae), Tambourissa Trichophylla Baker (Monimiaceae) Et Embelia Concinna Baker (Myrsinaceae)," Les Theses En Ligen De L'Institut National Polytechnique De Toulouse (INPT), Apr. 20, 2007.
Sandra Gallori, Anna Rita Bilia, Nadia Mulinacci, Carlo Bicchi, Patrizia Rubiolo, Franco Francesco Vinceri, "Identification of Volatile Constituents of Tambourissa Leptophylla," Planta Med, vol. 67, No. 3, pp. 290-292, 2001.
European Patent Office Non-Patent Literature Reference Number XP002561458, "Boise de Bombarde" Encyclopedia Online De La Flore a La Reunion, Nov. 14, 2007.
European Patent Office Non-Patent Literature Reference Number XP002561459, "New Decleor Vitaroma Lift Total Neck & Decollete Gel-Cream," Aug. 18, 2007.
P, Forgacs, O. Buffard, J.F. Desconclois, aA Jehanno, J. Provost, R. Tiberghien, A. Touche, "Phytochemical Studies and Biological Activities of Plants Endemic of the Islands of Reunion and Mauritius," Plant Med Phytother, vol. 15, No. 2, pp. 80-91, 1981.
Vidushi S. Neergheen, Theeshan Bahorun, Ling-Sun Jen, and Okezie L. Arooma, "Bioefficacy of mauritian endemic medicinal plants: Assessment of their phenolic contents and antioxidant potential," Pharmaceutical Biology, vol. 45, No. 1, pp. 9-17, Jan. 1, 2007.
Database WPI Week 200558 Thomson Scientific, London, GB; AN 2005-571536 XP002561460 & WO 2005/077349 A (Otsuka Pharm Co Ltd).
Birgit Schittek, Maren Paulmann, Ilknur Senyurek, Heiko Steffan, "The role of antimicrobial peptides in human skin and in skin infectious diseases," Infectious Disorders—Drug Targets, vol. 8, No. 3, pp. 135-143, Sep. 1, 2008.
English Translation of Official Action for JP 2011-529477, issued Jan. 21, 2014.
English Translation of Description for JP2007-186457 (machine translation).
English Translation of Claims for JP2007-186457 (machine translation).
English Translation of Abstract for JP2007-186457 (machine translation).
English Translation of Relevant Parts of JP2007-186457.

* cited by examiner

*Primary Examiner* — Qiuwen Mi

(57) ABSTRACT

Medicaments or cosmetic compositions for the treatment or alleviation of skin or mucous membrane diseases or disorders related to an enhanced level of anti-microbial peptides or proteins comprising *Tambourissa* plant extracts, which may comprise polyphenols.

9 Claims, 3 Drawing Sheets

COMPOSITIONS FOR SKIN DISEASE OR DISORDERS

1. FIELD OF THE INVENTION

This invention relates to medicaments and cosmetic compositions comprising *Tambourissa* plant extracts that in turn comprise polyphenols for the treatment or alleviation of skin or mucous membrane diseases or disorders related to an enhanced level of anti-microbial peptides or proteins. This invention also relates to processes for preparing a *Tambourissa* plant extract, the extract itself, and uses of the extract.

2. BACKGROUND OF THE INVENTION

The *Tambourissa* genus belongs to the Monimiaceae family and comprises about 43 species found throughout the western islands of the Indian Ocean, such as Madagascar, Comoros and the Mascarenes islands (Mauritius and Reunion). The various *Tambourissa* species tend to show endemic specificity as most of them are localized in only one island and in only one habitat.

*Tambourissa trichophylla* (Baker) growths in Madagascar and Comoros. It is a tree of from about 5 meters to about 12 meters high. The leaves are opposite, oblong to lanceolate, from 8 to 20 cm long, dentate on the upper part. Male flowers are 5-6 mm in diameter, axillaris or terminal, from 1.5 to 3 cm long. Fruits are globes, about 4 cm in diameter, with coriaceus pericarp and numerous drupes. In Madagascar, this plant is called Amborahasa or Ambora and is traditionally used in health care, for instance for scar improvement and keloids (bark) or oral care (tea leaves as mouthwash).

Other *Tambourissa* species are also used in traditional treatments: crushed fresh leaves of *Tambourissa microphylla* are directly applied onto the skin for wound healing action, *Tambourissa religiosa* is used for tissue repair and *Tambourissa capuronii* (leaves crushed with liquid vegetal waxes) helps for dandruff treatment.

*Tambourissa trichophylla* is known to contain polyphenols and flavonoids, including epicatechin, nicotiflorin and rutin (Thesis of A. Lhuillier, L'Iinstitut National Polytechnique de Toulouse, 2007).

Polyphenols are a group of chemical substances found in plants, characterized by the presence of more than one phenol unit or building block per molecule. Polyphenols are generally classified as hydrolyzable tannins (gallic acid esters of glucose and other sugars) and phenylpropanoids, such as lignins, flavonoids, and condensed tannins. Polyphenols have been shown to have antioxidant characteristics with potential health benefits.

Flavonoids are widely distributed in plants and help plants carry out many functions including helping in the production of yellow or red/blue pigmentation in flowers and helping protect against attack by microbes and insects. Flavonoids have a widespread distribution in plants, come in a great variety and generally have low human toxicity. Flavonoids have been referred to as "nature's biological response modifiers" because of strong experimental evidence suggesting that flavonoids have an ability to modify the body's reaction to allergens, viruses, and carcinogens. Some flavenoids show anti-allergic, anti-inflammatory, anti-microbial and anti-cancer activity.

Rutin, also called rutoside, is a citrus flavonoid glycoside having a structure similar to the flavonol quercetin and the disaccharide rutinose. It can be found in *Ruta graveolens*, buckwheat, the leaves and petioles of *Rheum* species, as well as other sources.

Rutin can combine with cations: in humans, it attaches to iron ions, $Fe^{+2}$, preventing iron from binding to hydrogen peroxide and from creating free-radical cellular damage. Rutin is also an antioxidant, and therefore can play a role in inhibiting some cancers. Rutin is also an anti-inflammatory agent. Rutin strengthens blood vessels, decreases the permeability of cell walls and acts as a vasodilatator. It can also act on edema in blood vessels and so decrease thrombosis risk. Rutin can help to decrease the cytoxicity of oxygenated DTL cholesterol, which may be one of the factors responsible for the development of atherosclerosis.

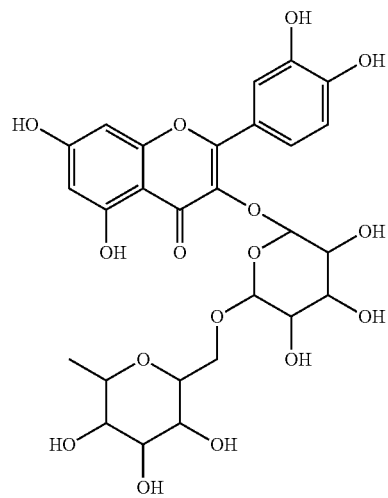

Rutin (quercetin-3-rutinoside)

Epicatechin is also a flavonoid and is a major polyphenolic component of green tea (*Camellia sinensis*) and may also be found in other species. Epicatechin has been shown to be an anti-oxidant, to improve cardiovascular function, to increase blood flow in the brain and to be active against hepatotropic viruses.

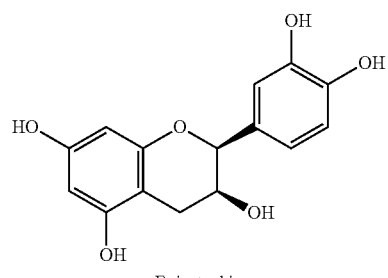

Epicatechin

Nicotiflorin is a flavonoid glycoside that can be found as such or as kaempferol-3-O-rutinoside glycosides in almonds (*Prunus dulcis*), green tea (*Camellia sinensis*), *Carthamus tinctorius*, *Pogonatherum crinitum*, *Centaurea hierapolitana*, *Microcos paniculata*, etc. Research on this compound has shown interesting properties with respect to its anti-oxidant potential, activity on blood circulation improvement. It is also a fibroblast growth promoter or can participate to anti-itching or to sunscreen activity. A composition containing nicotiflorin is claimed for wrinkles prevention by inducing collagen synthesis and inhibiting collagenase.

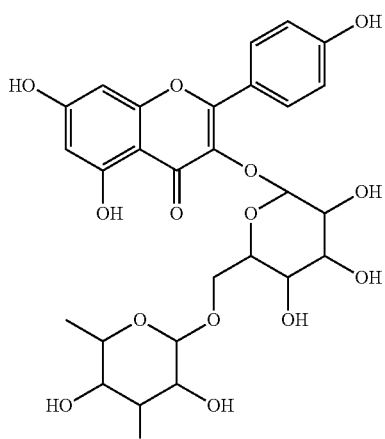

Nicotiflorin (kaempferol-3-O-β-D-rutinoside)

Antimicrobial peptides or proteins (or AMPs, also called host defense peptides) are broad-spectrum antibiomicrobial compounds and correspond to one of the primary mechanisms used by the multiple epithelial surfaces (more specifically skin) in the early stages of immune defense. AMPs include α- or β-defensin, RNase-7, S100-protein psoriasin or cathelicidin LL-37. The antimicrobial activity deals with Gram positive and Gram negative bacteria but also with fungi and viruses. The production of antimicrobial peptides or proteins by human skin occurs constitutively but seems also modulated after infection, inflammation or injury. Some skin diseases show altered expression of AMPs. For example their levels are increased in psoriatic lesions and decreased for atopic lesions (atopic dermatitis patients).

Cathelicidin is a cationic antimicrobial peptide expressed in most of the circulating immune cells (monocytes, leukocytes, neurophils etc) and also in epidermal keratinocytes. Cathelicidin is produced in various epithelia like skin or mucous membranes but also in sweat glands and sebocytes of the skin or scalp. hCAP18—human Cathelicidin Anti-Microbial Peptide of 18 kDa—comprises a cathelin-like domain and a C-terminal peptide called LL-37 (a peptide beginning with 2 leucine residues that is 37 amino acids long). The activity of cathelicidin is controlled by enzymatic processing of the proform (hCAP18) to a mature peptide (LL-37), which is induced by a proteolytic process involving kallikreins (such as Stratum corneum tryptic enzyme also called SCTE or kallikrein-5, S Stratum corneum chemotryptic enzyme also called SCCE or kallikrein-7).

In healthy skin, epidermal keratinocytes express low amounts of cathelicidin. On infection or barrier disruption, cathelicidin is strongly induced and is either released by neutrophils or may be stored by keratinocytes in lamellar bodies. In case of wound healing, cathelicidin participates of course to microbial defense but also to the skin repair process as it activates pro-inflammatory cytokines synthesis, chemotaxis of immune cells, angiogenesis and proteoglycan expression. In rosacea, increased cathelicidin expression in the LL-37 peptide form has been observed—along with kallikreins activity activation. Abnormal AMP expression also exists in psoriasis as cathelicidin has been shown to be increased in psoriatic lesional skin.

U.S. Pat. No. 7,718,618 to Gallo et al., issued May 18, 2010, discloses the use of cathelicidin or related synthetic peptides for anti-microbial activity, U.S. Pat. No. 7,777,000 to Gallo et al., issued Aug. 17, 2010, describes anti-viral activity and such in dermatitis, PCT Patent Publication No. WO 2004/067025 (also published as U.S. Pat. No. 7,452,864 to Ståle-Bächdal, issued Nov. 18, 2008) discloses its use in wound healing by causing cell proliferation and regeneration. European Patent Application No. 1,358,888 (also published as U.S. Publication Number 2006/0275303) discloses its use in angiogenesis induction. U.S. Publication No. 2008/0038374 describes the upregulation of cathelicidin and the subsequent effect on diseases, for example with Vitamin D and via sphingosylphosphoryl choline. PCT Patent Publication No. WO 2008/060362 (also published as U.S. Publication No. 2009/0318534) describes cathelicidin inhibitors—comprising antisense or ribozyme molecule or a vitamin D3 antagonist—and their use in rosacea and acne. The disadvantage of the use of these inhibitors, however, is that antisense oligonucleotides and ribozyme molecules are not readily available and many vitamin D antagonists, such as e.g. cortisone, have severe side effects.

Rosacea is a chronic inflammatory disease, generally occurring on the face, which affects about 45 millions people worldwide. It corresponds to vascular disorder and is characterized by telangiectasia (visible hemorrhagic dilated blood capillaries near the skin surface), erythema, papules, and pustules primary in the central areas of the face combined with frequent burning and itching sensations. Rosacea affects mostly Caucasians of mainly northwestern European descent, and concerns both sexes, but is almost three times more common in women, and has a peak age of onset between 30 and 60.

The existing rosacea therapeutics, which may be administered topically or administered systemically, include antibiotics, such as tetracycline, minocycline, erythromycin and doxycyline, azetromycin; anti-infectives, like azelaic acid, nadifloxacin, sodium sulfacetamide and metronidazole; anti-inflammatories with folic acids, nicotinamide and zinc oxide; Keratolysis activators, for example benzoyl peroxide, resorcinol and salicylic acid; and retinoids. These compounds and their formulations, however, are not always in rosacea and acne treatment.

Topical applications of metronidazole—cream or lotion with 0.75% to 1% active compound—are the most frequent treatment and have been shown to be effective when applied once or twice daily for 8-12 weeks. Some side effects related with use of metronidazole, including dry skin, skin redness or irritation, may occur.

Rosacea has multiple origins and may have causes like heredity, neurological disorders, gastric issues and other causes. Main causes that can be alleviated by topical treatment include: (a) an over-expression of active forms of anti-microbial peptides (cathelicidins) and related enzymes, involved in the maintenance of an infectious status leading to skin chronic inflammation or being favorable to skin inflammation chronicity; (b) a vascular defect, which contributes to impaired capillary neoangiogenesis with frequent hemorrhagic characteristics, leading to the weakening of a skin that naturally tends to be thin and reactive; (c) inflammation, initially elusive but steadily increasing to become persistent with flush and blush phenomena; and (d) an inflammatory process depending to environmental conditions such as UVs or free radicals.

SUMMARY OF THE INVENTION

The principal object of the invention therefore is to provide an alternative new and possibly more advantageous compound or medicament for the treatment of skin or mucous membrane diseases related to an enhanced level of AMPs, to chronic or induced inflammation and to angiogenesis impairment.

Another object of the invention is to provide a cosmetic composition for the alleviation of skin or mucous membrane disorders related to an enhanced level of AMPs, to chronic or induced inflammation and to angiogenesis impairment.

A further objective of the present invention is to provide a method of treating diseases related to an enhanced level of AMPs with the medicament or cosmetic of the invention.

Another objective of the present invention is a method of treating diseases or disorders, especially skin or mucous membrane diseases or disorders, related to an enhanced level of AMPs with a *Tambourissa* plant extract, which may be a *Tambourissa trichophylla* plant extract, especially a leaf extract.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the invention provides a medicament, especially a topical medicament, for the treatment of skin diseases or mucous membrane diseases comprising a *Tambourissa* plant extract.

The present invention is further directed to a cosmetic composition comprising a *Tambourissa* plant extract for the treatment of skin or mucous membrane disorders both related to an enhanced level of anti-microbial peptides or proteins, to chronic or induced inflammation and to angiogenesis impairment.

DETAILED DESCRIPTION OF THE PREFERRED EMBODIMENTS OF THE INVENTION

Figure 1:
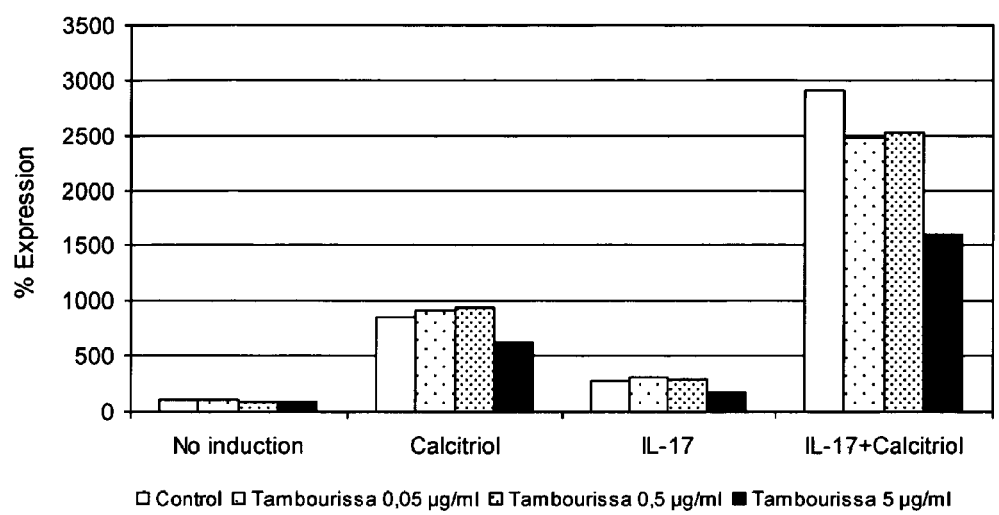
FIG. 1 shows modulation of expression in the Cathelicidin gene (CAMP) by the *Tambourissa* plant extracts of Example 4 and Table 3.
Figure 2:
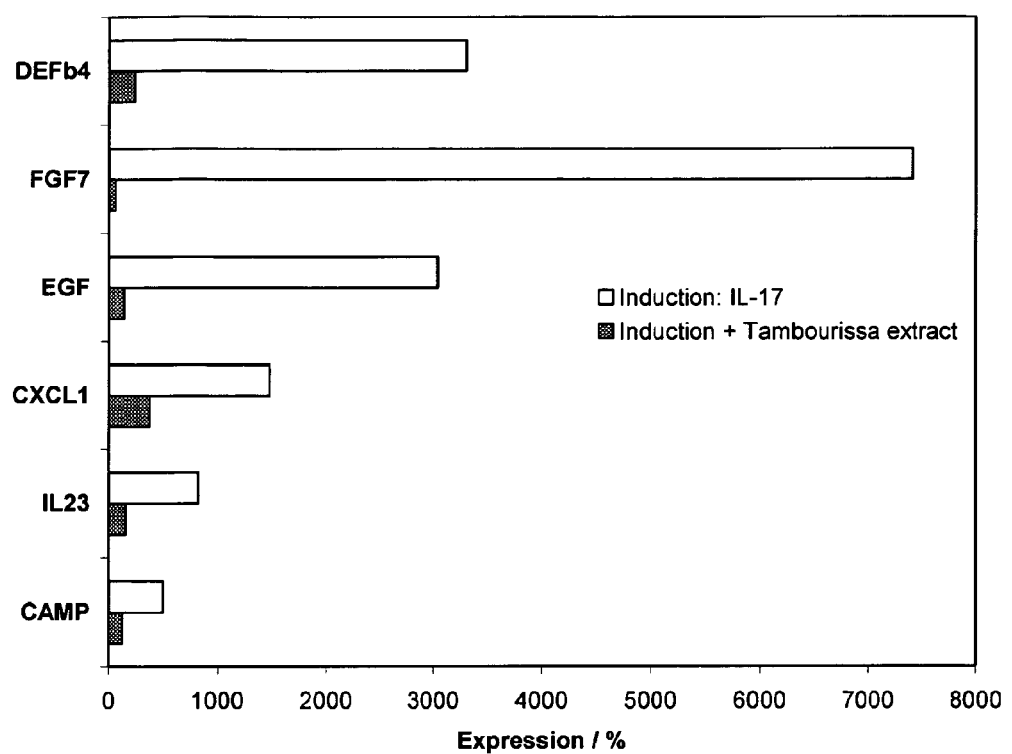
FIG. 2 show modulation of angiogenic factors by the *Tambourissa trichophylla* leaf extracts of Example 6 and Table 7. Induction is achieved by IL-17 only; the results of the *Tambourissa* plant extracts (Ambora) are displayed against a control.
Figure 3:
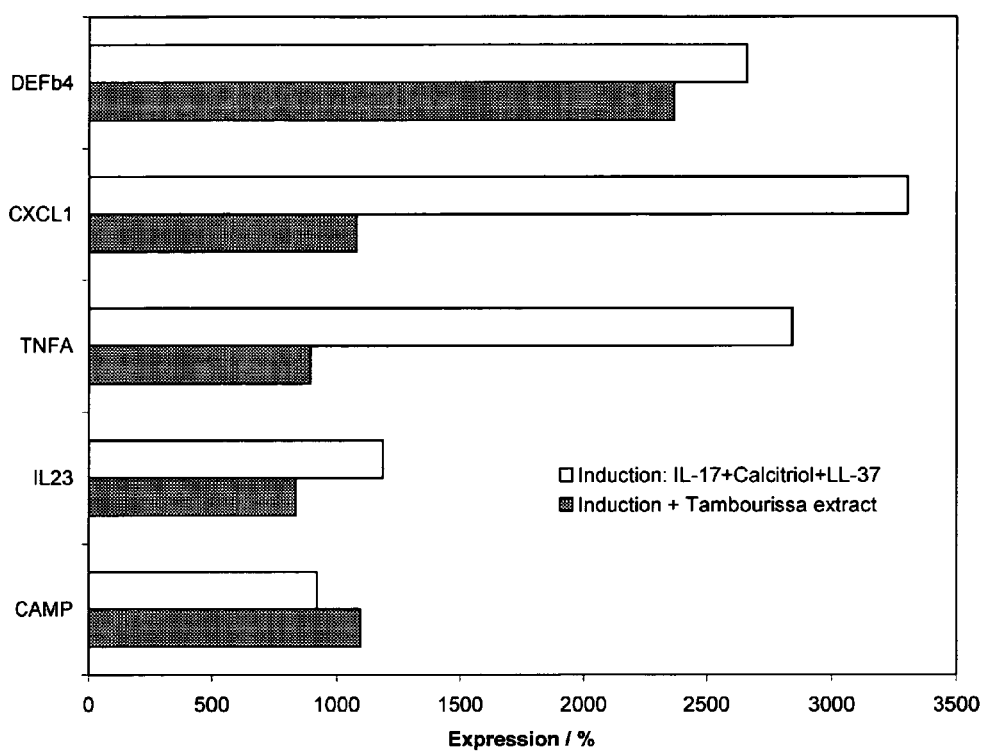
FIG. 3 shows modulation of angiogenic factors by the *Tambourissa trichophylla* leaf extracts of Example 6 and Table 7. Induction is achieved by IL-17+ and Calictriol+ LL37. The results of the *Tambourissa* plant extracts (Ambora) are displayed against a control.

Reference will now be made in detail to the presently preferred embodiments of the invention.

The invention comprises a medicament or cosmetic agent comprising a *Tambourissa* plant extract for the treatment of skin diseases or mucous membrane diseases or a cosmetic composition comprising a *Tambourissa* plant extract for the treatment of skin or mucous membrane disorders both related to an enhanced level of anti-microbial peptides or proteins, to chronic or induced inflammation and to angiogenesis impairment.

*Tambourissa* extracts according to the invention are extracts of plants of the *Tambourissa* species, which include, but are not limited to, *Tambourissa trichophylla, Tambourissa microphylla, Tambourissa religiosa* and *Tambourissa capuronii*. Plant extracts of *Tambourissa trichophylla* are preferred.

The medicament or cosmetic composition of the invention can comprise an extract of all parts of the plant(s) and may also comprise mixtures of *Tambourissa* plant extracts. In a preferred embodiment of the invention, the medicament or cosmetic composition may comprise an extract of the leaves of *Tambourissa trichophylla*. In a more preferred embodiment of the invention, the *Tambourissa* extract comprises polyphenols.

Preferred polyphenols of the invention are a group of chemical substances originally found in plants, characterized by the presence of more than one phenol unit or building block per molecule. Polyphenols are generally grouped as hydrolysable tannins (gallic acid esters of glucose and other sugars) and phenylpropanoids, such as lignins, flavonoids, and condensed tannins. Preferred polyphenols of the invention are flavonoids, and most preferred polyphenols are rutin, nicotiflorin, epicatechin and mixtures of these polyphenols.

The medicament or cosmetic composition of the invention comprises a *Tambourissa* plant extract, preferably a *Tambourissa trichophylla* extract, especially preferred a *Tambourissa trichophylla* leaf extract modulating, i e inhibiting and/or reducing, antimicrobial peptides or proteins (AMPs). In a preferred embodiment of the invention the medicament or cosmetic composition comprises *Tambourissa* extracts comprising polyphenols modulating, i.e. inhibiting and/or reducing, anti-microbial peptides or proteins (AMPs). AMPs include α- or β-defensin, RNase-7, S100-protein psoriasin and the cathelicidin in pro- or active form (LL-37). In a preferred embodiment of the invention, the inhibition and/or reduction of cathelicidin may be achieved in its pro or its activated form. Transformation of the pro-form may also be inhibited through inhibiting and/or reducing kallikrein synthesis. In a preferred embodiment of the invention the medicament or cosmetic composition it also modulates, i.e. reduces and/or inhibits, kallikrein synthesis.

Skin or mucous membrane diseases or disorders related to an enhanced level of anti-microbial peptides or proteins are include, but are not limited to, rosacea, acne, couperosis, erythrosis, telangiectasia, herpes, mouth infections, vaginal infections and/or sebaceous microbial infections, baby rash, dandruff, skin redness and/or skin blotchiness, atopic dermatitis, psoriasis, acanthosis, solar erythemas, after shave irritation, and itching.

The medicament of the invention may be used in the treatment of skin or mucous membrane diseases such as rosacea, acne, couperosis, erythrosis, telangiectasia, herpes, mouth infections, vaginal infections and/or sebaceous microbial infections, baby rash, dandruff, skin redness, skin blotchiness, atopic dermatitis, psoriasis, acanthosis, solar erythemas, after shave irritation, or itching. The cosmetic composition of the invention may be used for alleviating skin or mucous membrane disorders related to an enhanced level of anti-microbial peptides or proteins such as disorders associated with rosacea, acne, couperosis, erythrosis, telangiectasia, herpes, mouth infections, vaginal infections and/or sebaceous microbial infections, atopic dermatitis, psoriasis, acanthosis, or solar erythemas. The medicament or cosmetic composition of the invention may be used to treat or alleviate baby rash, dandruff, skin redness and/or skin blotchiness, after shave irritation, or itching. As cathelicidin has anti-microbial, anti-fungal, and anti-viral activity, the invention may also be used in the regulation of microbial, fungal and viral diseases of the skin, scalp and mucous ecosystem (oral or vaginal mucosa, for example), especially maintenance or modulation following or associated with inflammatory responses.

Whether the dosage regimen of the invention depends on the severity of the symptoms and may be determined by a dermatologist or other medical personnel.

The medicament or cosmetic composition of the invention may also have anti-inflammatory activity, especially when it comprises the *Tambourissa* plant extract disclosed below. The medicament or cosmetic composition of the invention can be destined to regulate epidermal, dermal, scalp or mucous membrane tissue homeostasis. Homeostasis is defined in Roche Lexikon Medizin Edition 5.0 (2003 Elsevier, online version in German) as the self-regulation of a biological system (such as the scalp or mucous membrane tissue system) which is in a dynamic equilibrium, e.g., to ensure resistance against changing environmental conditions. Accordingly, the invention may be used to restore and/or support the equilibrium of the skin against environmental and/or pathological conditions.

Inflammation is one of the first responses of the immune system to infection or irritation. Inflammation is stimulated by chemical factors released by injured cells and serves to establish a physical barrier against the spread of infection, and to promote healing of any damaged tissue following the clearance of pathogens. Chemical factors produced during inflammation (such as histamine, bradykinin, serotonin, leukotrienes, and prostaglandins) sensitize pain receptors, cause vasodilation of the blood vessels, and attract phagocytes, especially neutrophils. Neutrophils then trigger other parts of the immune system by releasing factors that will attract other leukocytes and lymphocytes. The inflammatory response may be characterized by redness, heat, swelling, pain and possible dysfunction of the organs or tissues affected by the inflammation.

Prolonged inflammation, known as chronic inflammation, leads to a progressive shift in the type of cells that are present at the site of inflammation and is characterized by simultaneous destruction and healing of the tissue from the inflammatory process due to persistent acute inflammation due to non-degradable pathogens, persistent foreign bodies, or autoimmune reactions. Autoimmune reactions can be linked to the involvement of lymphocytes and their specific differentiation towards different inducers into Th1, Th2 and/or Th17 leading to emphasizing some specific mediators, including Interleukine-1 (IL-1), IL-4 and IL-17. Psoriasis may be a mixed Th17/Th1 disease whereas atopic dermatitis may be a mixed Th17/Th2 disease.

The medicament or cosmetic composition of the invention is also active for inflammation modulation and the regulation of the inflammation drifts, for example in infections, chronic or induced inflammation, and aging. For instance the invention can reduce the synthesis of various pro-inflammatory agents in both inflammation pathways dealing with Cyclooxygenase (COX), Lipoxygenase (LOX) and with the subsequent formation of inflammatory messages (Prostaglandin-2, Leukotrienes, etc.). The invention is also active in regulating interleukins, especially the impact of the interleukin-17 factor, nitric oxide and free radicals production.

The invention is also useful for treating sensitive skin and the disorders associated with acute inflammatory conditions or auto-immune diseases, such as, but not limited to, atopic dermatitis, psoriasis, acanthosis, baby rash, solar erythemas, after shave irritation, and itching.

The medicament or cosmetic composition of the invention is active for angiogenesis regulation, more especially in downregulating the pro-angiogenic factors and upregulating the anti-angiogenic factors. The medicament or cosmetic composition can thus be used for the treatment or alleviation of rosacea, couperosis, erythrosis, telangiectasia, skin redness and blotchiness.

A medicament is a pharmaceutical composition comprising at least one active compound or drug destined for diagnosis or therapy. A medicament may influence the state or functioning of the body or affect the state or functioning of pathogens, parasites or xenobiotics with the aim of their removal. A medicament may also aim at substituting body compounds or fluids. The medicament (or cosmetic composition) of the invention can be administered in any form by any effective route, including, e.g., oral, parenteral, enteral, intravenous, intraperitoneal, topical, transdermal (e.g., using any standard patch), ophthalmic, nasally, local, non-oral, such as aerosal, via inhalation, subcutaneous, intramuscular, buccal, sublingual, rectal, vaginal, intra-arterial, and intrathecal, and any other useful and appropriate method of administration. Topical administration is preferred. The invention can be administered alone, or in combination with any ingredient(s), active or inactive.

The medicament or cosmetic composition of the present invention can be formulated into known forms such as pharmaceutical or cosmetic compositions or compositions used as food supplements or as part of a medical device. The formulations may be liquid or solid formulations such as, without limitation, normal and enteric coated tablets, capsules, pills, powders, granules, elixirs, tinctures, solution, suspensions, suppositories, syrups, solid and liquid aerosols, emulsions, pastes, creams, ointments, milks, gels, salves, serums, foams, shampoos, sticks or lotions.

Preference is given to a pharmaceutical or cosmetic composition in a form of topical pharmaceutical or cosmetic composition such as an aqueous solution, a white or colored cream, ointment, milk, gel, salve, serum, foam, shampoo, stick, cream, paste, or lotion.

The medicament or cosmetic composition of the present invention can be further combined with any other suitable additive or pharmaceutically or cosmetically acceptable carrier. Such additives include any of the substances already mentioned, as well as any of those used conventionally, such as those described in Remington: The Science and Practice of Pharmacy (Gennaro and Gennaro, eds, 20th edition, Lippincott Williams & Wilkins, 2000); Theory and Practice of Industrial Pharmacy (Lachman et al., eds., 3rd edition, Lippincott Williams & Wilkins, 1986); and Encyclopedia of Pharmaceutical Technology (Swarbrick and Boylan, eds., 2nd edition, Marcel Dekker, 2002). These materials are referred to herein as "pharmaceutically or cosmetically acceptable carriers" to indicate they are combined with the active drug or compound and can be administered safely to a subject for therapeutic or cosmetic purposes.

The dosage of the medicament or cosmetic composition of the invention can be selected with reference to the other and/or the type of disease or disorder and/or the disease or disorder status in order to provide the desired therapeutic or cosmetic activity. These amounts can be determined routinely for a particular patient or person to be cosmetically treated, where various parameters are utilized to select the appropriate dosage (e.g., type of disease or disorder, age of patient, disease or disorder status, patient health, weight, etc.), or the amounts can be relatively standard and can be easily determined by a person skilled in the art. The amount of the administered medicament or cosmetic composition can vary widely according to such considerations as the particular compound and dosage unit employed, the mode and time of administration, the period of treatment, the age, sex, and general condition of the patient or person to be treated, the nature and extent of the condition treated, the rate of drug or compound metabolism and excretion, the potential drug combinations and drug-drug interactions, and the like.

The medicament or cosmetic composition may comprise any amount of *Tambourissa* extract. A medicament or cosmetic composition comprising the dried extract of *Tambourissa trichophylla* leaves as described below in an amount of from about 0.01% to about 5% by weight of the total composition is preferred. An amount of from about 0.1% to about 1% by weight, is more preferred, and from about 0.3% to about 0.5% by weight is most preferred.

The medicament or cosmetic composition according to the invention may be administered once or more, preferably up to three, and most preferably up to two times per day. Nevertheless, it may in some cases be advantageous to deviate from the amounts specified, depending on body weight, individual reactions to the active ingredient, type of pharmaceutical preparation and time or interval over which the administration is effected. For instance, less than the aforementioned minimum amounts may be sufficient in some cases, while the upper limit specified has to be exceeded in other cases. In the case of administration of relatively large amounts, it may be advisable to divide these into several individual doses over the day.

The medicament or cosmetic composition of the present invention can also be combined with at least one further active substance or plant extract e.g. substances or plant extracts usually employed for pharmaceutical, dermatological or cosmetic use. Further active substances include, but are not limited to, desquamating and/or moisturizing agents, UV filtering or blocking agents, depigmenting or propigmenting agents, antiglycation agents, anti-inflammatory agents, antimicrobial agents, agents stimulating the synthesis of dermal, epidermal, hair or nail macromolecules and/or preventing the degradation thereof, agents stimulating the differentiation of keratinocytes, muscle relaxants, antipollution and/or anti-free radical agents, slimming agents, agents acting on the microcirculation, agents acting on the energy metabolism of the cells, tightening agents, agents preventing the loss or stimulating the growth of hair, agents preventing grey or white hair, or a mixture thereof. Preferably the combination is contained in a topically dermatological composition.

The medicament or cosmetic composition may also contain at least one additional rosacea-effective agent, for example metronidazole, clindamycin, doxycycline, erythromycin, minocycline hydrochloride, tetracycline hydrochloride, azelaic acid, sodium sulfacetaminde, nicotinamide, benzyl peroxide, salicylic acid, adapalene, isotretinoid, tazarotene, or tretinoid.

The invention further comprises a process for preparing *Tambourissa* extracts. According to the invention these extracts are of plants of the *Tambourissa* species, which include, but are not limited to, *Tambourissa trichophylla, Tambourissa microphylla, Tambourissa religiosa* and *Tambourissa capuronii*. *Tambourissa trichophylla* is preferred. The extraction can be performed on all parts of the plant(s), but the leaves of *Tambourissa trichophylla* are preferred.

The extraction can be done by standard extraction methods. Preferably the extraction is carried out with a polar solvent applicable for extraction. Leaves are first extracted with a polar solvent, e.g. mixtures of water and alcohol, optionally several times. The obtained solution is then mixed, the alcohol is preferably removed and the precipitate is removed by filtration. In another embodiment of the invention the whole polar solvent is removed and the residue is extracted with water. The obtained polar phase is extracted with a non polar solvent e.g. ethyl acetate or heptane, to remove the waxes, essential oils, pigments and most of the non polar molecules. After phase separation the solvent of the remaining polar phase is removed in order to obtain a dry extract comprising polyphenols. Optionally, the extract may be dried by adding water followed by freeze-drying.

A process for preparing a *Tambourissa trichophylla* leaf extract may comprise the steps of: (a) extracting the leaves with a polar solvent mixture of water and alcohol; (b) removing the alcohol; (c) filtering the solution; and (d) extracting the obtained polar solution with a non-polar solvent to separate the extract.

The polar solvent used for extraction is preferably alcohol or a mixture of water and alcohol wherein the alcohol is preferably ethanol. The ratio of the volume between water and alcohol can be from about 50:50 to about 90:10, preferably about 70:30.

The invention further comprises a *Tambourissa trichophylla* leaf extract. The extract according to the invention can be prepared as described above or as disclosed in Example 1.

An extract according to the invention is normally a dry extract. Nevertheless the extract can also be used as solution, i.e. the final drying step of the extraction process may omitted, or the dry extract may be mixed with other liquid active compounds, or the dry extract may be incorporated in an optimized carrier to form a solution or other fluid state like an emulsion or dispersion. The extract may also be encapsulated and the encapsulated extract may be dispersed in a fluid carrier.

Dry plant extracts that contain polyphenols in an amount of more than about 10% by weight with respect to the total plant extract are preferred, and extracts having more than about 15% by weight are more preferred. Extracts having from about 15% to about 45% by weight polyphenols are highly preferred, and extracts having from about 15% to about 35% by weight polyphenols are especially preferred. Preferred polyphenols comprise flavonoids, and in a preferred embodiment of the invention the plant extract comprises from about 0.01% to about 20% by weight rutin, nicotiflorin and epicatechin. Most preferably, rutin may be present in an amount of from about 0.01% to about 5% by weight, epicatechin may be present in an amount of about 0.01% to about 10% by weight and nicotiflorine may be present in an amount of from about 0.01% to about 5% by weight of the extract. While extracts comprising all three compounds are preferred, extracts containing one or two of these compounds may also be useful in the invention.

The invention further comprises the use of the *Tambourissa* extracts, preferably *Tambourissa trichophylla* extracts, and more preferably *Tambourissa trichophylla* leaf extracts, in the modulation of antimicrobial peptides or proteins, especially in the inhibition and/or reduction of cathelicidin and/or kallikrein synthesis. The invention further comprises the use of the *Tambourissa* plant extracts for the treatment of skin diseases or disorders or mucous membrane diseases or disorders related to an enhanced level of anti-microbial peptides or proteins. It further comprises the use of the *Tambourissa* plant extracts as anti-inflammatory agents and as a regulator of angiogenesis.

The following examples will illustrate some embodiments and advantages of the invention without limiting the general nature and scope of the invention.

Example 1

Extraction Process

Crushed dry leaves of *Tambourissa trichophylla* are extracted with a mixture of ethanol and water (in a volume ratio of 70:30). The mixture is stirred and heated at a temperature below 60° C. for a period of about 30 minutes to about 1 hour to perform the extraction. The solid plant material is removed, and ethanol is then removed leading to a precipitate, which is filtered out of the remaining aqueous solution. The aqueous solution is then treated by liquid-liquid extraction with ethyl acetate. The acetate fraction is retained for acetate distillation and the consequent aqueous solution is freeze-dried.

The final extract is characterized by thin layer chromatography (TLC), using HPLC standard methods and spectrophotometry. The final composition shows a content of 19% to 21% by weight of polyphenols and less than 2% by weight rutin and nicotiflorine. The presence of epicatechin is also detected by TLC.

Example 2

Cosmetic Formulation Examples

Emulsions containing various concentrations of *Tambourissa trichophylla* leaf extract were prepared in accordance with Example 1. The emulsion concentrations are set forth in Table 1. Phases A and B of the emulsions were weighed separately. The separate phases (A & B) were heated to 80° C. and mixed under high stirring A to B. The mixture was cooled down to 35° C. while stirring and component C was added. The compounds listed members of component D were mixed until a transparent solution was obtained and component D was then added to the formulation. The final formulation was cooled down to room temperature while stirring continued.

The final compositions were cosmetic oil in water emulsions: excipient (A) was white and formulations containing extract according to Example 1 (B & C) were beige to beige-orange.

TABLE 1

Emulsions of Example 2

|   | INCI Name | A Excipient | B Excipient + 0.3% extract | C Excipient + 0.5% extract |
|---|---|---|---|---|
| A | Glyceryl Stearate + PEG-100 Stearate | 2.00 | 2.00 | 2.00 |
|   | Cetearyl Alcohol + Cetearyl Glucoside | 3.00 | 3.00 | 3.00 |
|   | Octyldodecyl Myristate | 4.00 | 4.00 | 4.00 |
|   | Isohexadecane | 3.00 | 3.00 | 3.00 |
|   | Dicaprylyl Ether | 3.00 | 3.00 | 3.00 |
|   | C8/C10 Triglyceride | 2.00 | 2.00 | 2.00 |
|   | Phenoxyethanol + Methylparaben + Isopropylparaben + Isobutylparaben + Butylparaben | 0.80 | 0.80 | 0.80 |
| B | Water | 100.00—S amount of other excipients | 100.00—S amount of other excipients | 100.00—S amount of other excipients |
|   | Glycerin | 1.50 | 1.50 | 1.50 |
| C | Cyclomethicone | 3.00 | 3.00 | 3.00 |
| D | Water | — | 5.00 | 5.00 |
|   | Butylene glycol | — | 1.5 | 2.5 |
|   | Tambourissa Trichophylla Leaf Extract | — | 0.3 | 0.5 |
|   | TOTAL (g) | 100.00 | 100.00 | 100.00 |

Example 3

Anti-Inflammatory Activity on prostaglandin-2 (PGE-2)

A test was performed on HUVEC (human umbilical vein endothelial cells). HUVEC were incubated for 24 hours without (control) or with various concentrations of the extract from to example 1, and in presence of an inducer: VEGF (venous endothelial growth factor). PGE-2 levels were measured in the medium by the ELISA method. Significance was evaluated by the Student test.

TABLE 2

Inhibitory activity of Tambourissa trichophylla leaf extract according to Example 1 on PGE-2 synthesis by HUVEC

|   |   | PGE-2 (pg/µg proteins) | Variation towards control + VEGF (%) | Significance |
|---|---|---|---|---|
| Control without VEGF | | 1.84 | — | — |
| Control with VEGF | | 10.78 | — | — |
| Tambourissa extract in presence of VEGF | 0.5 µg/ml | 11.66 | +8% | NS |
|  | 1 µg/ml | 6.11 | −43%** | $p < 0.01$ |
|  | 5 µg/ml | 8.91 | −17%** | $p < 0.01$ |

**significantly different from the control with VEGF ($p < 0.01$)

The *Tambourissa* plant extract in the medicament or cosmetic composition of the invention can significantly modulate the cyclooxygenase pathway and therefore can have positive influence on inflammation state and thus be efficient in the treatment or alleviation of atopic dermatitis, psoriasis, acanthosis, baby rash, solar erythemas, after shave irritation, and itching.

Example 4

Inhibition of CAMP (Cathelicidin Anti-Microbial Peptide) Gene

The capacity of the extract according the invention to inhibit the release of antimicrobial peptide cathelicidin was investigated. The expression of CAMP (Cathelicidin Anti-Microbial Peptide) gene coding for hCAP18 (further actived into LL37) was performed using RT-qPCR technology on mRNA extracted from keratinocytes NHEK (074). The Culture medium was Keratinocyte-SFM (source: Invitrogen 17005075) supplemented with Epidermal Growth Factor (EGF) (0.25 ng/ml) (Invitrogen 10450-013), Pituitary extract (PE) (25 µg/ml) (Invitrogen 13028-014), and Gentamycin (25 µg/ml) (Sigma G1397). The assay medium is Keratinocyte-SFM (Invitrogen 17005075) supplemented with Gentamycin (25 µg/ml) (Sigma G1397).

The extract obtained was solubilized in DMSO and tested at concentrations of 0.05, 0.5 and 5 µg/ml.

The keratinocytes were seeded in 24 well plates, in a culture medium. After 24 hours of pre-incubation, the culture medium was removed and replaced by assay medium containing or not containing (control) the test compound and the cells were incubated for 24 hours. After incubation the inducers were added and incubated for 48 hours. Tested inducers are calcitriol (Vitamin D3, (Sigma D-1530) at 10 M) or IL-17 ((R&D Systems 317-IL-050) at 10 ng/ml).

At the end of the incubation time, the supernatants were collected and the cells were washed in phosphate buffered saline (PBS) solution (Invitrogen 14190094), 300 µl of TriReagent was added and the cells were immediately frozen at −80° C. Total RNA was extracted from each sample using Tri-reagent according to supplier directions. Potential contaminant traces of DNA were removed using the DNA free system (Ambion ref 1906). The reverse-transcription of mRNA was conducted in presence of oligo(dT) and Superscript II reversetranscriptase (Invitrogen). The PCR (Polymerase Chain Reactions) were performed in triplicate using the «LightCycler®» system (Roche Molecular Systems Inc.) in accordance with the protocol recommended by the supplier. This system allows rapid and powerful PCR reactions, after determining the analysis conditions of the tested primers. It consists in two components: (a) a thermo-cycler: optimized for rapid PCR applications; allowing extremely rapid thermal transfers within the reaction mixture, and (b) a fluorimeter: allowing constant fluorescence measurement of the intercalating dye SYBR Green I; a dye that specifically binds to double-stranded DNA during the elongation cycle (detection wavelength: 521 nm).

The following primers couples were used to amplify the fragment corresponding to the selected marker. In this experiment, Liver glyceraldehyde 3-phosphate dehydrogenase gene (G3PDH) was used as a reference marker. The incorporation of fluorescence in amplified DNA was measured continuously during the PCR cycles.

TABLE 3

Regulation of CAMP gene expression by keratinocytes (s. FIG. 1)

| Treatment with Tambourissa | % expression | | | |
|---|---|---|---|---|
| trichophylla leaf extract | Control without inducer | Calcitriol (Vitamin D) | IL-17 | Calcitriol + IL-17 |

TABLE 3-continued

| Control | 100 | 852 | 277 | 2910 |
|---|---|---|---|---|
| 0.05 µg/ml | 112 | 911 | 310 | 2486 |
| 0.5 µg/ml | 92 | 938 | 288 | 2521 |
| 5 µg/ml | 98 | 629 | 168 | 1604 |

Calcitriol or IL-17 and combination thereof highly stimulated the expression of the gene CAMP coding for hCAP-18/LL37. The extract according to Example 1 (*Tambourissa trichophylla* leaf extract or "Ambora") dose-dependently reduces cathelicidin gene coding for LL37. This reduction can reach 40% (compared to control with induction) in case of IL-17 induction and 27% for calcitriol induction.

The *Tambourissa* plant extract in the medicament or cosmetic composition of the invention can therefore be active in cathelicidin-linked diseases or disorders and used for the treatment and alleviation of diseases or disorders such as rosacea, psoriasis or vaginal infections.

Example 5

Clinical Study

The objective of this study was to evaluate the efficacy of compositions containing different concentrations of the extract according to the invention. The test was performed on two formulations containing 0.3% and 0.5% of the extract, respectively (formulations B and C from example 2). The test was performed versus a placebo (formulation A of example 2). The study was performed on 3 groups of 15 volunteers. Each group tested a different product. Evaluation was performed at the beginning of the study and after 28 and 56 days of twice-daily applications of the formulations A, B or C on the face.

Evaluation was scored with structured scales of the redness density and the density of micro-vessels by a dermatologist (scaled from 1 to 4). Microcirculation variations were tested with Doppler Laser® and gave results about the skin perfusion (or capillary flux). Macrographs were also performed for visual effect illustration. General inclusion criteria for volunteers' recruitment concerned healthy subjects, women from 18 to 65 years old, with slight Rosacea characteristics on the face. Under the conditions of this study under dermatologist control, the cutaneous tolerance of all the formulations was good after 28 or 56 days of twice daily use. The results are shown in Table 4.

TABLE 4

Variation of the dermatologist scoring after 28 and 56 days of twice-daily use of the test product (comparison with the initial condition)

| | | Variation of redness intensity | Significance (Wilcoxon test) | Variation of density of apparent microvessels | Significance (Wilcoxon test) |
|---|---|---|---|---|---|
| Formulation with 0.3% Tambourissa extract— Formulation B | Δ D28 | −0.4 | p = 0.031 Yes | −0.1 | p = 0.500 No |
| | Δ D56 | −0.5 | p = 0.008 Yes | −0.1 | p = 1.000 No |
| Formulation with 0.5% Tambourissa extract— Formulation C | Δ D28 | −0.6 | p = 0.016 Yes | −0.2 | p = 0.500 No |
| | Δ D56 | −0.7 | p = 0.008 Yes | −0.3 | p = 0.250 No |

According to dermatologist scoring, skin was less red after 28 or 56 days of use but no variation was noticed for microblood vessels density. A decrease in the thermal conductivity corresponds to a decrease of the cutaneous microcirculation (vasoconstriction), which would contribute to an anti-rosacea effect.

TABLE 5

Variation of the thermal conductivity after 28 and 56 days of twice-daily use of the test product (comparison with the initial condition)

| | Δ D28 | Significance | Δ D56 | Significance |
|---|---|---|---|---|
| Placebo— Formulation A | 4% | p = 0.892 No | −14% | P = 0.761 No |
| Formulation with 0.3% Tambourissa extract— Formulation B | −42%** | p = 0.01 Yes | −1% | P = 0.934 No |

TABLE 5-continued

Variation of the thermal conductivity after 28 and 56 days of twice-daily use of the test product (comparison with the initial condition)

|  | Δ D28 | Significance | Δ D56 | Significance |
|---|---|---|---|---|
| Formulation with 0.5% Tambourissa extract—Formulation C | −52%** | p = 0.032 Yes | −72%* | P = 0.05 Yes |

Significant decrease in microcirculation has been noticed with 0.3% formulation at D28 and with 0.5% formulation at D28 and D56. Significant variation was observed neither with placebo nor with 0.3% formulation at D56.

TABLE 6

Comparison between products

|  | Kinetics | Mean | Significance |  | Type of statistic test |
|---|---|---|---|---|---|
| 0.3% formulation vs placebo | Δ D28 | −83.82 | p = 0.404 | No | Dunett's test |
|  | Δ D56 | 28.80 | p = 0.903 | No | Dunett's test |
| 0.5% formulation vs placebo | Δ D28 | −189.46 | p = 0.034 | Yes | Dunett's test |
|  | Δ D56 | −222.20 | p = 0.014 | Yes | Dunett's test |
| 0.3% formulation vs 0.5% formulation | Δ D28 | 105.65 | p = 0.199 | No | Unpaired t test |
|  | Δ D56 | 251.01 | p = 0.05 | Yes | Unpaired t test |

The data showed a significantly higher activity on the microcirculation with 0.5% formulation product than with placebo at D28 and D56. The data also show a significantly higher activity on the microcirculation with 0.5% formulation product than with 0.3% formulation at D56. The decrease of skin redness and of the skin microcirculation makes formulations B and C, possible medicaments or cosmetic compositions comprising *Tambourissa* plant extract according to the invention, suitable for rosacea, erythrosis telangiectasis or skin redness/blotchiness treatment and/or alleviation.

Example 6

Modulation of Angiogenic Factors

The activity of the extract according to the invention was studied on pro-angiogenic factors expression by human keratinocytes. The activity of *Tambourissa* extract (5 µg/ml) was tested by RT-q-PCR technology on RNA extracted from keratinocytes NHEK K(074) stimulated by the following inducers: LL-37 (20 µg/ml), IL-17 (10 ng/ml), vitamin D3 (10-6M), and combinations thereof. The incorporation of fluorescence in amplified DNA was measured continuously during the PCR cycles. This resulted in a "fluorescence intensity" versus "PCR cycle" plot allowing the evaluation of a relative expression (RE) value for each marker. The value selected for RE calculations is the "output point" (Ct) of the fluorescence curve. For a considered marker, the highest is the cycle number; the lowest is the mRNA quantity.

The culture medium was Keratinocyte-SFM supplemented with Epidermal Growth Factor (EGF) 0.25 ng/ml, Pituitary extract (PE) 25 µg/ml, and Gentamycin 25 µg/ml. The assay medium was Keratinocyte-SFM supplemented with Gentamycin 25 µg/ml. The effects ("treated" versus "control" condition) were measured by the scale set forth in Table 7.

TABLE 7

Classification of Effects

| Relative expression (% of control) | Classification of the effects |
|---|---|
| >300% | Strong stimulation |
| >200% | Stimulation |
| >150% and <200% | Moderate stimulation, to be confirmed |
| <65% and >50% | Moderate inhibition |
| <50% and >30% | Inhibition |
| <30% | Strong inhibition |

The results are set forth in Table 8.

TABLE 8

Regulation of pro-angiogenic factor expression by keratinocytes

| | | IL-17 | | IL-17 + LL-37 + Vitamin D3 | |
|---|---|---|---|---|---|
| Gene abbreviation | Gene name | Control | Tambourissa extract | Control | Tambourissa extract |
| Moy HK | Moyenne Housekeeping | 100 | 100 | 100 | 100 |
| GAPDH | glyceraldehyde-3-phosphate dehydrogenase | 54 | 78 | 91 | 119 |
| EGF | Epidermal Growth Factor | 3037 | 140 | 135 | 230 |
| FGF7 | fibroblast growth factor 7 (FGF7) | 7413 | 61 | 159 | 336 |
| CXCL1 | Chemokine (C-X-C motif) ligand 1 | 1478 | 379 | 3304 | 1078 |
| TNFa | Tumor necrosis factor alpha precursor | 381 | 125 | 2842 | 894 |
| CAMP | Cathelicidin antimicrobial peptide | 502 | 124 | 921 | 1092 |
| DEFb4 | Defensin beta 4 | 330313 | 23643 | 265961 | 236775 |
| IL23 | Homo sapiens interleukin 23 | 825 | 156 | 1185 | 839 |

The *Tambourissa* test plant extract is the *tambourissa trichophylla* leaf extract of Example 1. Under these experimental conditions, the *Tambourissa* plant extract of the invention partially reverse the effects of LL-37, IL-17 and vitamin D3, tested alone or in association, on the expression of angiogenic markers. In addition, the results also suggest that *Tambourissa* plant extract is an inhibitor of IL-17 (reduction of the impact of this pro-inflammatory agent).

The medicaments or cosmetic compositions comprising *Tambourissa* plant extract in accordance with the invention are thus understood to have a decreasing effect on pro-angiogenic gene expression rendering them suitable for rosacea, couperosis, erythrosis, telangiectasia, skin redness and blotchiness treatment and/or alleviation.

The purpose of the above description is to illustrate some embodiments of the present invention without implying a limitation. It will apparent to those skilled in the art that various modifications and variations may be made in the apparatus or procedure of the invention without departing from the scope or spirit of the invention.

What is claimed is:

1. A method for treating rosacea comprising the step of administering a topical composition comprising *Tambourissa* plant extract to a patient in need thereof, wherein the topical composition comprises from about 0.01% to about 10% by weight of the *Tambourissa* plant extract.

2. The method of claim 1, wherein the *Tambourissa* plant extract is an extract of *Tambourissa trichophylla, Tambourissa microphylla, Tambourissa religiosa* or *Tambourissa capuronii*.

3. The method of claim 1, wherein the *Tambourissa* plant extract is an extract of *Tambourissa trichophylla*.

4. A method for treating skin redness comprising the step of administering a topical composition comprising *Tambourissa* plant extract to a patient in need thereof, wherein the topical composition comprises from about 0.01% to about 10% by weight of the *Tambourissa* plant extract.

5. The method of claim 4, wherein the *Tambourissa* plant extract is an extract of *Tambourissa trichophylla, Tambourissa microphylla, Tambourissa religiosa* or *Tambourissa capuronii*.

6. The method of claim 4, wherein the *Tambourissa* plant extract is an extract of *Tambourissa trichophylla*.

7. A method for treating skin disorders or mucous membrane disorders associated with conditions selected from the group consisting of couperosis, erythrosis, telangiectasia, herpes, mouth infections, vaginal infections, sebaceous microbial infections, baby rash, dandruff, skin blotchiness, atopic dermatitis, psoriasis, acanthosis, solar erythemas, after shave irritation, and itching comprising the step of administering a topical composition comprising *Tambourissa* plant extract to a patient in need thereof, wherein the topical composition comprises from about 0.01% to about 10% by weight of the *Tambourissa* plant extract.

8. The method of claim 7, wherein the *Tambourissa* plant extract is an extract of *Tambourissa trichophylla, Tambourissa microphylla, Tambourissa religiosa* or *Tambourissa capuronii*.

9. The method of claim 7, wherein the *Tambourissa* plant extract is an extract of *Tambourissa trichophylla*.

* * * * *